United States Patent
Ionescu et al.

(10) Patent No.: US 8,614,313 B2
(45) Date of Patent: Dec. 24, 2013

(54) PHARMACEUTICAL COMPOSITIONS COMPRISING FORMS OF 5-AZACYTIDINE

(75) Inventors: Dumitru Ionescu, Ann Arbor, MI (US); Peter Blumbergs, Royal Oak, MI (US); Gary L. Silvey, Overland Park, KS (US)

(73) Assignee: Pharmion LLC, Summit, NJ (US)

( * ) Notice: Subject to any disclaimer, the term of this patent is extended or adjusted under 35 U.S.C. 154(b) by 0 days.

(21) Appl. No.: 13/587,768

(22) Filed: Aug. 16, 2012

(65) Prior Publication Data

US 2013/0059809 A1    Mar. 7, 2013

Related U.S. Application Data

(60) Division of application No. 12/787,214, filed on May 25, 2010, which is a continuation of application No. 11/458,365, filed on Jul. 18, 2006, now Pat. No. 7,772,199, which is a continuation of application No. 11/052,615, filed on Feb. 7, 2005, now Pat. No. 7,078,518, which is a division of application No. 10/390,578, filed on Mar. 17, 2003, now Pat. No. 6,887,855.

(51) Int. Cl.
*A61K 31/7068* (2006.01)
*C07H 19/12* (2006.01)

(52) U.S. Cl.
CPC ............ *A61K 31/7068* (2013.01); *C07H 19/12* (2013.01)
USPC .......................................... 536/28.3; 514/42

(58) Field of Classification Search
None
See application file for complete search history.

(56) References Cited

U.S. PATENT DOCUMENTS

| | | | |
|---|---|---|---|
| 3,350,388 A | 10/1967 | Sorm et al. |
| 3,817,980 A | 6/1974 | Vorbruggen et al. |
| 3,891,623 A | 6/1975 | Vorbruggen et al. |
| 4,082,911 A | 4/1978 | Vorbruggen |
| 4,209,613 A | 6/1980 | Vorbruggen |
| 5,700,640 A | 12/1997 | Voss et al. |
| 5,872,104 A | 2/1999 | Vermeulen et al. |
| 5,985,864 A | 11/1999 | Imai et al. |
| 6,642,206 B2 | 11/2003 | Ramasamy et al. |
| 6,723,728 B2 | 4/2004 | Hu et al. |
| 6,753,426 B2 | 6/2004 | Zhang et al. |
| 6,887,855 B2 | 5/2005 | Ionescu et al. |
| 6,943,249 B2 | 9/2005 | Ionescu et al. |
| 7,038,038 B2 | 5/2006 | Ionescu et al. |
| 7,078,518 B2 | 7/2006 | Ionescu et al. |
| 7,084,268 B1 | 8/2006 | Chiba et al. |
| 7,132,552 B2 | 11/2006 | Dolitzky et al. |
| 7,189,740 B2 | 3/2007 | Zeldis |
| 7,192,781 B2 | 3/2007 | Luna et al. |
| 7,642,247 B2 | 1/2010 | Daifuku et al. |
| 7,700,770 B2 | 4/2010 | Ionescu et al. |
| 7,759,481 B2 | 7/2010 | Gavenda et al. |
| 7,772,199 B2 | 8/2010 | Ionescu et al. |
| 7,858,774 B2 | 12/2010 | Ionescu et al. |
| 8,058,424 B2 | 11/2011 | Ionescu et al. |
| 8,211,862 B2 | 7/2012 | Ionescu et al. |
| 2004/0162263 A1 | 8/2004 | Sands et al. |
| 2005/0075508 A1 | 4/2005 | Fukae et al. |
| 2006/0063735 A1 | 3/2006 | Redkar et al. |
| 2006/0069060 A1 | 3/2006 | Redkar et al. |
| 2006/0074046 A1 | 4/2006 | Redkar et al. |
| 2006/0128654 A1 | 6/2006 | Tang et al. |
| 2007/0190022 A1 | 8/2007 | Bacopoulos et al. |
| 2008/0057086 A1 | 3/2008 | Etter et al. |
| 2008/0182806 A1 | 7/2008 | Pizzorno |
| 2009/0286752 A1 | 11/2009 | Etter et al. |
| 2010/0035354 A1 | 2/2010 | Bigatti et al. |
| 2010/0036112 A1 | 2/2010 | Henschke et al. |
| 2010/0062992 A1 | 3/2010 | Redkar et al. |
| 2010/0210833 A1 | 8/2010 | Jungmann et al. |
| 2010/0292180 A1 | 11/2010 | Ionescu et al. |
| 2010/0298253 A1 | 11/2010 | Ionescu et al. |
| 2010/0311683 A1 | 12/2010 | Beach et al. |
| 2011/0042247 A1 | 2/2011 | Kocherlakota et al. |
| 2011/0092694 A1 | 4/2011 | Ionescu et al. |
| 2011/0201800 A1 | 8/2011 | Cherukupally et al. |
| 2011/0245485 A1 | 10/2011 | De Ferra et al. |
| 2012/0029181 A1 | 2/2012 | Ionescu et al. |
| 2012/0245342 A1 | 9/2012 | Ionescu et al. |
| 2013/0059810 A1 | 3/2013 | Ionescu et al. |

FOREIGN PATENT DOCUMENTS

| | | |
|---|---|---|
| CZ | 114716 | 11/1964 |
| CZ | 116297 | 4/1965 |
| DE | 1922702 | 11/1969 |
| DE | 2012888 | 9/1971 |

(Continued)

OTHER PUBLICATIONS

U.S. Appl. No. 13/587,770, filed Aug. 16, 2012, Ionescu et al.

(Continued)

*Primary Examiner* — Eric S Olson
(74) *Attorney, Agent, or Firm* — Jones Day

(57) ABSTRACT

The invention provides novel polymorphic and pseudopolymorphic crystalline forms of 5-azacytidine, along with methods for preparing said forms, wherein 5-azacytidine is represented by the formula:

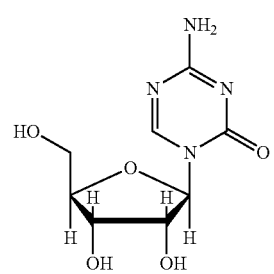

The invention also includes pharmaceutical compositions comprising said forms.

13 Claims, 8 Drawing Sheets

(56) References Cited

FOREIGN PATENT DOCUMENTS

| FR | 2123632 | 9/1972 |
|---|---|---|
| GB | 1227691 | 4/1971 |
| GB | 1227692 | 4/1971 |
| WO | WO 2004/082619 | 9/2004 |
| WO | WO 2006/034154 | 3/2006 |
| WO | WO 2008/088779 | 7/2008 |
| WO | WO 2009/016617 | 2/2009 |
| WO | WO 2011/014541 | 2/2011 |

OTHER PUBLICATIONS

U.S. Appl. No. 13/489,307, filed Jun. 5, 2012, Ionescu et al.
Ault, Techniques and Experiments for Organic Chemistry, 6th ed., University Science Books, 59-60 (1998).
Beers et al. (eds.), Chapter 142, Section 11, in The Merck Manual of Diagnosis and Therapy, 18th Edition, pp. 1114-1116 (2006).
Beisler et al., "Chemistry of Antitumor Triazine Nucleosides. An Improved Synthesis of Dihydro-5-Azacytidine," J. Carbohydrates Nucleosides Nucleotides, 4(5): 281-99 (1977).
Beisler et al., "Synthesis and Antitumor Activity of Dihydro-5-azacytidine, a Hydrolytically Stable Analogue of 5-Azacytidine," J. Med. Chem., 20(6): 806-12 (1977).
Beisler, "Isolation, Characterization, and Properties of a Labile Hydrolysis Product of the Antitumor Nucleoside, 5-Azacytidine," J. Med. Chem., 21(2): 204-08 (1978).
Bergy et al., "Microbiological Production of 5-Azacytidine II. Isolation and Chemical Structure," Antimicrobial Agents and Chemotherapy, 625-30 (1966).
Bond et al., "Controlling Crystal Architecture in Molecular Solids: the Supramolecular Approach," in Supramolecular Organization and Materials Design, Jones & Rao eds., Cambridge University Press, Chapter 12, pp. 391-443 (2002).
Braga et al., "Making Crystals From Crystals: a Green Route to Crystal Engineering and Polymorphism," Chemical Communications, 3635-45 (2005).
Brittain, "Polymorphism: Pharmaceutical Aspects," in Encyclopedia of Pharmaceutical Technology, 2nd Edition, vol. 3, Swarbrick & Boylan eds., pp. 2239-2249 (2002).
Byrn et al., "Drugs as Molecular Solids," in Solid-State Chemistry of Drugs, 2nd Edition, pp. 3-43 (1999).
Cabri et al., "Polymorphisms and Patent, Market, and Legal Battles: Cefdinir Case Study," Organic Process Research & Development, 11: 64-72 (2007).
Chan, K.K. et al., "5-Azacytidine Hydrolysis Kinetics Measured by High-Pressure Liquid Chromatography and 13C-NMR Spectroscopy," J. Pharm. Sci., 68(7): 807-12 (1979).
Chen et al., "Highly Efficient Regioselective Synthesis of 5'-O-lauroyl-5-azacytidine Catalyzed by Candida Antarctica Lipase B," Appl. Biochem. Biotechnol., 151: 21-28 (2008).
Day et al., "An Assessment of Lattice Energy Minimization for the Prediction of Molecular Organic Crystal Structures," Crystal Growth & Design, 4(6): 1327-40 (2004).
Dean, Analytical Chemistry Handbook, pp. 10.23-10.26 (1995).
Dintaman et al., "Inhibition of P-Glycoprotein by D-α-Tocopheryl Polyethylene Glycol 1000 Succinate (TPGS)," Pharmaceutical Research, 16(10): 1550-1556 (1999).
Dover et al., "5-Azacytidine Increases HbF Production and Reduces Anemia in Sickle Cell Disease: Dose-Response Analysis of Subcutaneous and Oral Dosage Regimens," Blood, 66(3): 527-532 (1985).
Garcia-Manero et al., "A Pilot Pharmacokinetic Study of Oral Azacitidine," Leukemia, 22: 1680-84 (2008).
Garcia-Manero et al., "Phase 1 Study of Oral Azacitidine in Myelodysplastic Syndromes, Chronic Myelomonocytic Leukemia, and Acute Myeloid Leukemia," J. Clin. Oncol., 29(18): 2521-27 (2011).
Gaubert et al., "Unnatural Enantiomers of 5-Azacytidine Analogues: Synthesis and Enzymatic Properties," Nucleosides, Nucleotides & Nucleic Acids, 20(4-7): 837-40 (2001).
Giron, "Investigations of Polymorphism and Pseudo-Polymorphism Pharmaceuticals by Combined Thermoanalytical Techniques," Journal of Thermal Analysis and Calorimetry, 64: 37-60 (2001).
Giron, "Thermal Analysis and Calorimetric Methods in the Characterisation of Polymorphs and Solvates," Thermochimica Acta, 248: 1-59 (1995).
Guillory, "Generation of Polymorphs, Hydrates, Solvates, and Amorphous Solids," in Polymorphism in Pharmaceutical Solids, pp. 183-226 (1999).
Gut et al., "Aza Analogs of Pyrimidine and Purine Bases of Nucleic Acids," in Advances in Heterocyclic Chemistry, vol. 1, Katritzky ed., pp. 189-251 (1963).
Hanka et al., "Microbiological Production of 5-Azacytidine I. Production and Biological Activity," Antimicrobial Agents and Chemotherapy, 619-24 (1966).
Hilfiker et al., in Polymorphism in the Pharmaceutical Industry, pp. 1-19, 287-308 (2006).
Jain et al., "Polymorphism in Pharmacy," Indian 23(6): 315-29 (1986).
Jones et al., "Pharmaceutical Cocrystals: An Emerging Approach to Physical Property Enhancement," MRS Bulletin, 31: 875-79 (2006).
Khankari et al., "Pharmaceutical Hydrates," Thermochimica Acta, 248: 61-79 (1995).
Knapman, "Polymorphic Predictions: Understanding the Nature of Crystalline Compounds Can Be Critical in Drug Development and Manufacture," Modern Drug Discovery, 53-57 (2000).
Kornblith et al., "Impact of Azacytidine on the Quality of Life of Patients with Myelodysplastic Syndrome Treated in a Randomized Phase III Trial: A Cancer and Leukemia Group B Study," J. Clin Oncol., 20(10): 2441-52 (2002).
Kritz et al., "Pilot Study of 5-Azacytidine (5-AZA) and Carboplatin (CBDCA) in Patients with Relapsed/Refractory Leukemia," American Journal of Hematology, 51(2): 117-21 (1996).
Landgrebe, Organic Laboratory, 4th Edition, pp. 111-112 (1993).
Lin et al., "High Performance Liquid Chromatographic Analysis of Chemical Stability of 5-Aza-2'-deoxycytidine," J. Pharm. Sci., 70(11): 1228-32 (1981).
Morissette et al., "Elucidation of Crystal Form Diversity of the HIV Protease Inhibitor Ritonavir by High-Throughput Crystallization," Proc. Natl. Acad. Sci., 100(5): 2180-84 (2003).
New Experimental Chemistry Seminar, Basic Operation I, Japan Chemical Society, 3rd Print, pp. 318-327 (1978).
Niedballa et al., "A General Synthesis of N-Glycosides. V. Synthesis of 5-Azacytidines," J. Org. Chem., 39(25): 3672-74 (1974).
Notari et al., "Kinetics and Mechanisms of Degradation of the Antileukemic Agent 5-Azacytidine in Aqueous Solutions," J. Pharm. Sci., 64(7), 1148-57 (1975).
O'Neil et al. (eds.), The Merck Index, 13th Edition, p. 154-155 (2001).
O'Neil et al. (eds.), The Merck Index, 14th Edition, p. 150 (2006).
Piskala et al., "4-Amino-1-Beta-D-Ribofuranosyl-Triazin-2(1H)-one (5-azacytidine)," Nucleic Acid Chem., 1: 435-41 (1978).
Piskala et al., "Direct Synthesis of 5-Azapyrimidine Ribonucleosides," Nucleic Acids Research, Special Pub. No. 1: s17-20 (1975).
Piskala et al., "Nucleic Acids Components and Their Analogues. LI. Synthesis of 1-Glycosyl Derivatives of 5-Azauracil and 5-Azacytosine," Collect. Czech. Chem. Commun., 29: 2060-76 (1964).
Seddon, "Pseudopolymorph: A Polemic," Crystal Growth & Design, 4(6): 1087 (2004).
Silverman et al., "Randomized Controlled Trial of Azacitidine in Patients with the Myelodysplastic Syndrome: A Study of the Cancer and Leukemia Group B," J. Clin. Oncol., 20(10): 2429-40 (2002).
Skikne et al., "A Phase I, Open-Label, Dose-Escalation Study to Evaluate the Safety, Pharmacokinetics, and Pharmacodynamics of Oral Azacitidine in Subjects with Myelodysplastic Syndromes (MDS) or Acute Myelogenous Leukemia (AML)," Journal of Clinical Oncology (May 20, 2008 Supplement), 2008 ASCO Annual Meeting Proceedings (Meeting Date: May 30-Jun. 3, 2008), Part I, 2008,26(15S), poster # 7091 (2008).

(56) References Cited

OTHER PUBLICATIONS

Stavchansky et al., "Bioavailability in Tablet Technology," in Pharmaceutical Dosage Forms, Tablets, 2nd Edition, Revised and Expanded, vol. 2 of 3, Lieberman et al. eds., pp. 462-472 (1990).
Stoltz et al., "Development of an Oral Dosage Form of Azacitidine: Overcoming Challenges in Chemistry, Formulation, and Bioavailability," Blood, 48th ASH Annual Meeting (Meeting Date: Dec. 9-12, 2006), 108, poster # 4850 (2006).
Vippagunta et al., "Crystalline Solids," Advanced Drug Delivery Reviews, 48: 3-26 (2001).
Vogler et al., "5-Azacytidine (NSC 102816): A New Drug for the Treatment of Myeloblastic Leukemia," Blood, 48(3): 331-37 (1976).
Vorbruggen et al., "A New Simplified Nucleoside Synthesis," Chem. Ber., 114: 1279-86 (1981).
Vorbruggen et al., "Nucleoside Synthesis with Trimethylsilyl Triflate and Perchlorate as Catalysts," Chem. Ber., 114: 1234-55 (1981).
Vorbruggen et al., in Organic Reactions, vol. 55, 100 (L.A. Paquette ed., John Wiley & Sons, New York, 2000).
Ward et al., "An Oral Dosage Formulation of Azacitidine: A Pilot Pharmacokinetic Study," Journal of Clinical Oncology (Jun. 20, 2007 Supplement), 2007 ASCO Annual Meeting Proceedings (Meeting Date: Jun. 1-5, 2007), Part I, 25(18S), poster # 7084 (2007).
Winkley et al., "Direct Glycosylation of 1,3,5-Triazinones. A New Approach to the Synthesis of the Nucleoside Antibiotic 5-Azacytidine (4-Amino-1-β-D-ribofuranosyl-1,3,5-triazin-2-one) and Related Derivatives," J. Org. Chem., 35(2): 491-95 (1970).
Wittenburg et al., "A New Synthesis of Nucleosides," Zeitschrift fur Chemie, 4: 303-04 (1964) (with English translation).
Zaitseva et al., "Convergent Syntheses and Cytostatic Properties of 2-Chloro-2'-Deoxy-2'-Fluoroadenosine and its N7-Isomer," Bioorg. & Med. Chem. Lett., 5(24): 2999-3002 (1995).
Ziemba et al., "Development of Oral Demethylating Agents for the Treatment of Myelodysplastic Syndromes," American Association of Cancer Research, 100th Annual Meeting, Apr. 18-22, Abstract #3369 (2009).
Notice of Allowability dated May 4, 2012 in U.S. Appl. No. 12/729,116.
Notice of Allowance dated Sep. 20, 2011 in U.S. Appl. No. 12/729,116.
Office Action dated Aug. 1, 2011 in U.S. Appl. No. 12/466,213.
Opposition Brief dated Sep. 3, 2007 in Chile Application No. 2267-2005 (with English translation).
Final Office Action dated Mar. 6, 2012 in U.S. Appl. No. 12/787,214.
Non-Final Office Action dated Sep. 23, 2011 in U.S. Appl. No. 12/787,214.
Non-Final Office Action dated Jun. 5, 2013 in U.S. Appl. No. 12/787,214.
Notice of Allowance dated Apr. 25, 2013 in U.S. Appl. No. 13/587,770.

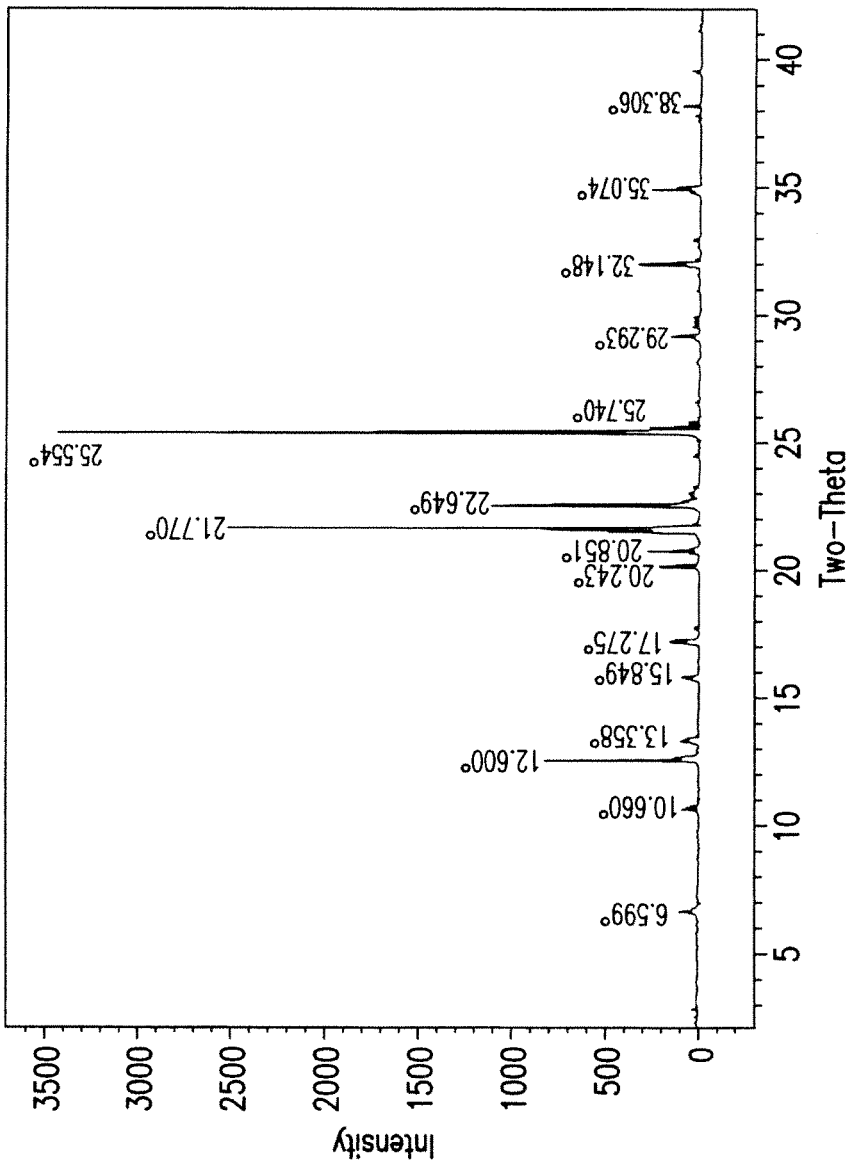

PHARMACEUTICAL COMPOSITIONS COMPRISING FORMS OF 5-AZACYTIDINE

RELATED APPLICATIONS

This application is a divisional of copending U.S. patent application Ser. No. 12/787,214, filed May 25, 2010, which is a continuation of U.S. patent application Ser. No. 11/458,365, filed Jul. 18, 2006, now U.S. Pat. No. 7,772,199, entitled, "Forms of 5-Azacytidine," which is a continuation of U.S. patent application Ser. No. 11/052,615, filed Feb. 7, 2005, now U.S. Pat. No. 7,078,518, entitled, "Forms of 5-Azacytidine," which is a divisional of U.S. patent application Ser. No. 10/390,578, filed Mar. 17, 2003, now U.S. Pat. No. 6,887,855, entitled, "Forms of 5-Azacytidine," the contents of all of which are incorporated by reference herein in their entireties.

FIELD OF THE INVENTION

The invention relates to polymorphic and pseudopolymorphic forms of 5-azacytidine (also known as azacitidine and 4-amino-1-β-D-ribofuranosyl-S-triazin-2(1H)-one), methods for preparing said forms, and pharmaceutical compositions comprising said forms. 5-azacytidine may be used in the treatment of disease, including the treatment of myelodysplastic syndromes (MDS).

BACKGROUND OF THE INVENTION

Polymorphs exist as two or more crystalline phases that have different arrangements and/or different conformations of the molecule in a crystal lattice. When a solvent molecule(s) is contained within the crystal lattice the resulting crystal is called a pseudopolymorph, or solvate. If the solvent molecule(s) within the crystal structure is a water molecule, then the pseudopolymorph/solvate is called a hydrate. The polymorphic and pseudopolymorphic solids display different physical properties, including those due to packing, and various thermodynamic, spectroscopic, interfacial and mechanical properties (See H. Brittain, Polymorphism in Pharmaceutical Solids, Marcel Dekker, New York, N.Y., 1999, pp. 1-2). Polymorphic and pseudopolymorphic forms of the drug substance (also known as the "active pharmaceutical ingredient" (API)), as administered by itself or formulated as a drug product (also known as the final or finished dosage form, or as the pharmaceutical composition) are well known and may affect, for example, the solubility, stability, flowability, fractability, and compressibility of drug substances and the safety and efficacy of drug products, (see, e.g., Knapman, K Modern Drug Discoveries, March 2000: 53).

5-azacytidine (also known as azacitidine and 4-amino-1-β-D-ribofuranosyl-1,3,5-triazin-2(1H)-one; Nation Service Center designation NSC-102816; CAS Registry Number 320-67-2) has undergone NCI-sponsored clinical trials for the treatment of myelodysplastic syndromes (MDS). See Kornblith et al., J. Clin. Oncol. 20(10): 2441-2452 (2002) and Silverman et al., J. Clin. Oncol. 20(10): 2429-2440 (2002). 5-azacytidine may be defined as having a formula of $C_8H_{12}N_4O_5$, a molecular weight of 244.20 and a structure of:

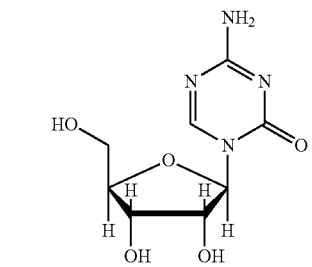

The polymorphic form of 5-azacytidine drug substance and drug product has never been characterized. It is an object of the present invention to characterize the polymorphic forms of 5-azacytidine.

SUMMARY OF THE INVENTION

It has been unexpectedly found that 5-azacytidine exists in at least eight different polymorphic and pseudopolymorphic crystalline forms (Forms I-VIII), in addition to an amorphous form. Form I is a polymorph found in prior art retained samples of 5-azacytidine drug substance. Form II is a polymorph found in some prior art retained samples of the 5-azacytidine drug substance; in those samples, Form II is always found in mixed phase with Form I. Form III is a hydrate, and is formed when prior art retained and current samples of the drug product are reconstituted with water to form a "slurry" prior to administration to the patient. Form VI is found in prior art retained samples of the 5-azacytidine drug product, either substantially free of other polymorphs, or in mixed phase with Form I.

The invention provides novel crystalline forms referred to as Form IV, Form V, Form VII and Form VIII. Forms I-VIII each have characteristic X-ray power diffraction (XRPD) patterns and are easily distinguished from one another using XRPD.

Also included in the present invention are methods for robustly and reproducibly synthesizing 5-azacytidine drug substance substantially as Form IV, Form V, or Form VIII. Also provided are methods for robustly and reproducibly synthesizing a Form I/VII mixed phase. The invention also provides pharmaceutical compositions comprising the various forms of 5-azacytidine together with one or more pharmaceutically acceptable excipients, diluents, or carriers.

BRIEF DESCRIPTION OF THE FIGURES

FIG. 8 presents the XRPD pattern of 5-azacytidine, Form VIII, labeled with the most prominent 2θ angles (Cu Kα radiation).

DETAILED DESCRIPTION OF THE PREFERRED EMBODIMENTS 5-azacytidine Crystalline Forms I-VIII It has been discovered that 5-azacytidine exists in at least eight different polymorphic and pseudopolymorphic crystalline forms, and also in an amorphous form.

Form I

A single sample of the 5-azacytidine drug substance was synthesized from 5-azacytosine and 1,2,3,5,-Tetra-O-acetyl-β-D-ribofuranose according to the prior art method provided in Example 1. The last step of this method is a recrystallization of the crude synthesis product from a DMSO/methanol co-solvent system. Specifically, the crude synthesis product is dissolved in DMSO (preheated to about 90° C.), and then methanol is added to the DMSO solution. The co-solvent mixture is equilibrated at approximately −20° C. to allow 5-azacytidine crystal formation. The product is collected by vacuum filtration and allowed to air dry.

Figure 1:
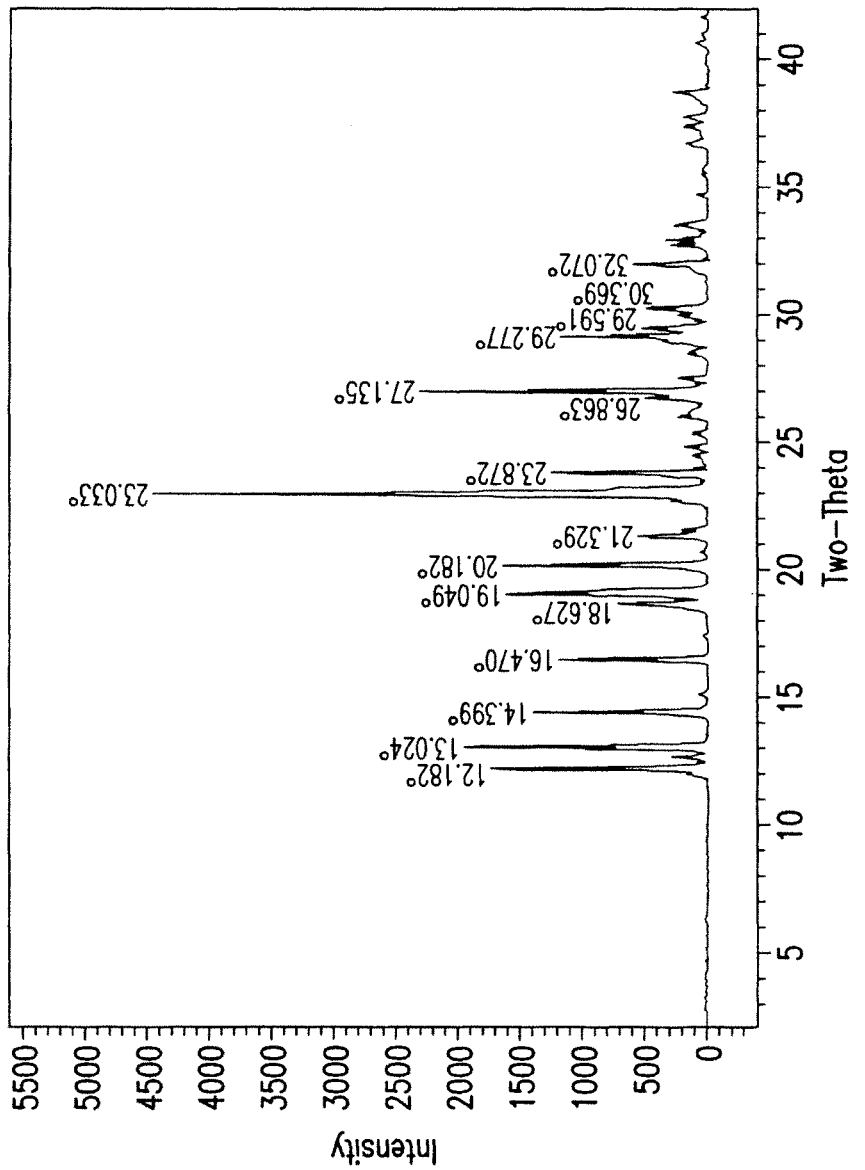
FIG. 1 presents the X-Ray Powder Diffraction (XRPD) pattern of 5-azacytidine, Form I, labeled with the most prominent 2θ angles (Cu Kα radiation).

The X-Ray Powder Diffraction (XRPD: see Example 5) pattern of the resulting 5-azacytidine is shown in FIG. 1 along with some of the 2θ values. Table 1 provides the most prominent 2θ angles, d-spacing and relative intensities for this material, which is designated as Form I.

TABLE 1

5-azacytidine Form I - the most prominent 2θ angles, d-spacing and relative intensities (Cu Kα radiation)

| 2θ Angle (°) | d-spacing (Å) | Relative Intensity |
|---|---|---|
| 12.182 | 7.260 | 39.1 |
| 13.024 | 6.792 | 44.1 |
| 14.399 | 6.146 | 31.5 |
| 16.470 | 5.378 | 27.1 |
| 18.627 | 4.760 | 16.0 |
| 19.049 | 4.655 | 35.9 |
| 20.182 | 4.396 | 37.0 |
| 21.329 | 4.162 | 12.4 |
| 23.033 | 3.858 | 100.0 |
| 23.872 | 3.724 | 28.0 |
| 26.863 | 3.316 | 10.8 |
| 27.135 | 3.284 | 51.5 |
| 29.277 | 3.048 | 25.6 |
| 29.591 | 3.016 | 11.5 |
| 30.369 | 2.941 | 10.8 |
| 32.072 | 2.788 | 13.4 |

Thermal analysis of Form I indicates that this form of 5-azacytidine is anhydrous. See Example 6.

Form II

Retained samples of the drug substance previously used to formulate the drug product in the NCI-sponsored Cancer and Leukemia Group B (CALGB) investigations (Phase 2 trial 8291 and Phase 3 trial 9221) for the treatment of MDS (Investigational New Drug (IND) 7574) were also analyzed by XRPD. The retained drug substance samples comprised either Form I, or a mixed phase of Form I and another polymorph: Form II. See Example 5.

Figure 2:
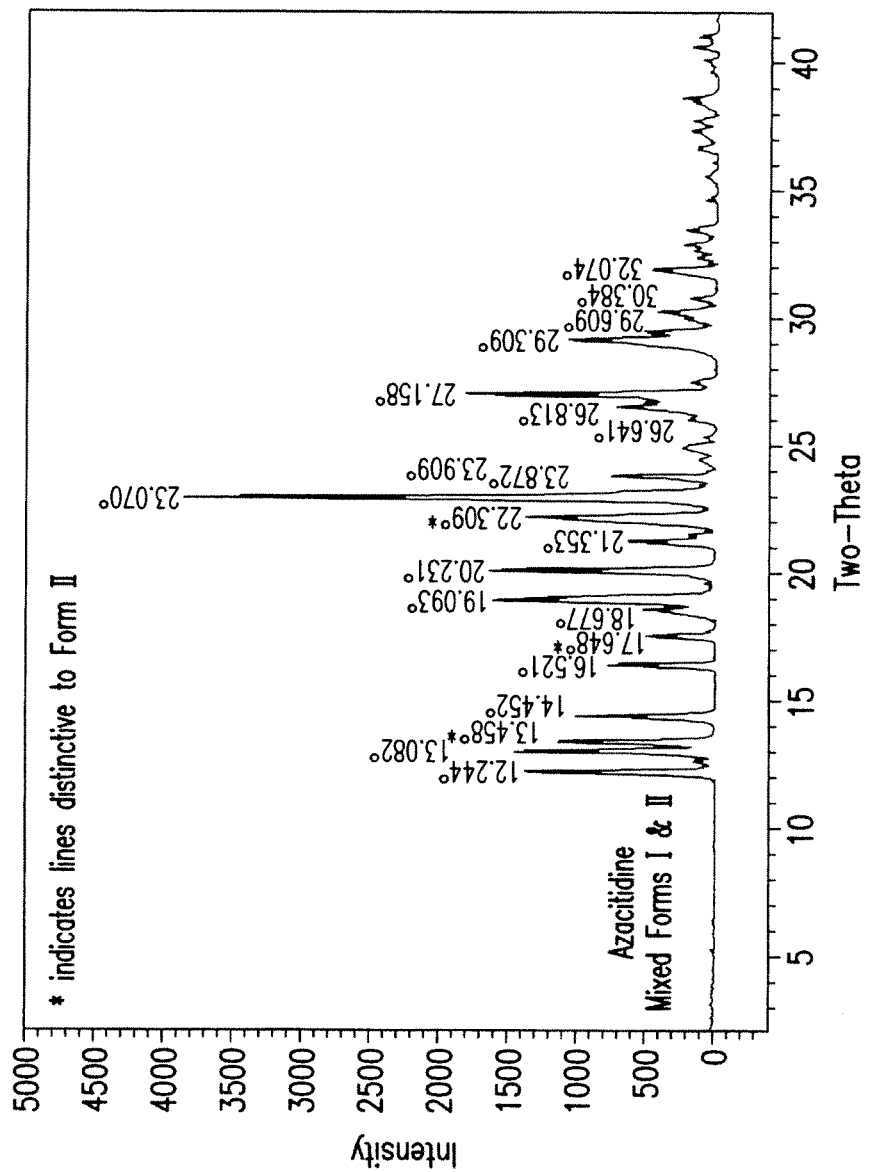
FIG. 2 presents the XRPD pattern of 5-azacytidine, mixed phase Form I and Form II, labeled with the most prominent 2θ angles (Cu Kα radiation).

The XRPD powder pattern of mixed phase Forms I and II is shown in FIG. 2 along with some of the 2θ values. Peaks distinctive to Form II are observed at 13.5, 17.6 and 22.3° 2θ. Table 2 provides the most prominent 2θ angles, d-spacing and relative intensities for this mixed phase.

TABLE 2

5-azacytidine, Mixed Phase Forms I and II - the most prominent 2θ angles, d-spacing and relative intensities (Cu Kα radiation)

| 2θ Angle (°) | d-spacing (Å) | Relative Intensity |
|---|---|---|
| 12.244 | 7.223 | 34.8 |
| 13.082 | 6.762 | 37.0 |
| 13.458* | 6.574 | 29.2 |
| 14.452 | 6.124 | 25.4 |
| 16.521 | 5.361 | 19.0 |
| 17.648* | 5.022 | 12.1 |
| 18.677 | 4.747 | 12.7 |
| 19.093 | 4.645 | 41.3 |
| 20.231 | 4.386 | 42.1 |
| 21.353 | 4.158 | 15.5 |
| 22.309* | 3.982 | 35.1 |
| 23.070 | 3.852 | 100.0 |
| 23.909 | 3.719 | 18.9 |
| 26.641 | 3.343 | 18.2 |
| 26.813 | 3.322 | 12.6 |
| 27.158 | 3.281 | 46.0 |
| 29.309 | 3.045 | 27.3 |
| 29.609 | 3.015 | 12.7 |
| 30.384 | 2.939 | 10.5 |
| 32.074 | 2.788 | 12.0 |

These results indicate that the prior art 5-azacytidine synthesis procedures for the drug substance produce either Form I substantially free of other forms, or a Form I/II mixed phase i.e. a solid material in which 5-azacytidine is present in a mixed phase of both Form I and Form II.

Thermal analysis of mixed phase Form I/II is presented in Example 6.

Form III

Figure 3:
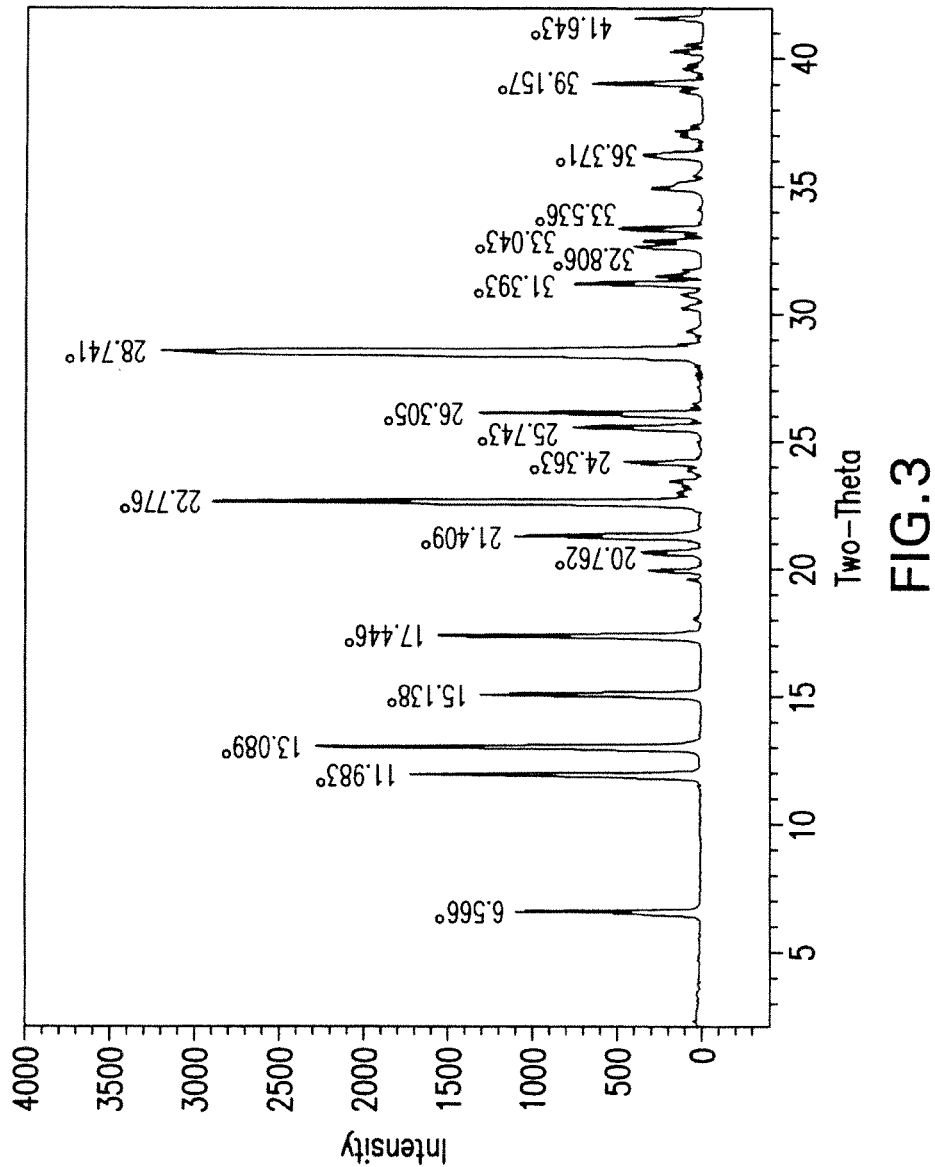
FIG. 3 presents the XRPD pattern of 5-azacytidine, Form III, labeled with the most prominent 2θ angles (Cu Kα radiation).

An additional crystalline form of 5-azacytidine, designated Form III, is found in slurries of 5-azacytidine. See Example 8. Moreover, it has been found that all forms of 5-azacytidine (including the 5-azacytidine in the prior art drug product) convert to Form III in water. See Example 8. Thus, reconstitution of the drug product used in the aforementioned NCI trials would have led to the formation of a saturated solution (or "slurry") in which the remaining solid 5-azacytidine was Form III. The XRPD powder pattern of Form III is shown in FIG. 3 along with some of the 2θ values. Table 3 provides the most prominent 2θ angles, d-spacing and relative intensities for this crystalline material. The XRPD powder pattern for Form III is distinctly different from that of all of the other forms of 5-azacytidine.

TABLE 3

5-azacytidine, Form III - the most prominent 2θ angles, d-spacing and relative intensities (Cu Kα radiation)

| 2θ Angle (°) | d-spacing (Å) | Relative Intensity |
|---|---|---|
| 6.566 | 13.450 | 32.9 |
| 11.983 | 7.380 | 52.5 |
| 13.089 | 6.758 | 71.0 |
| 15.138 | 5.848 | 38.9 |
| 17.446 | 5.079 | 48.2 |
| 20.762 | 4.275 | 10.8 |
| 21.049 | 4.147 | 34.8 |
| 22.776 | 3.901 | 89.5 |
| 24.363 | 3.651 | 13.7 |
| 25.743 | 3.458 | 22.8 |
| 26.305 | 3.385 | 39.9 |
| 28.741 | 3.104 | 100.0 |
| 31.393 | 2.847 | 22.5 |

TABLE 3-continued 5-azacytidine, Form III - the most prominent 2θ angles, d-spacing and relative intensities (Cu Kα radiation)

| 2θ Angle (°) | d-spacing (Å) | Relative Intensity |
|---|---|---|
| 32.806 | 2.728 | 11.8 |
| 33.043 | 2.709 | 10.1 |
| 33.536 | 2.670 | 15.1 |
| 36.371 | 2.468 | 11.0 |
| 39.157 | 2.299 | 19.3 |
| 41.643 | 2.167 | 12.1 |

Thermal analysis and proton ($^1$H) NMR spectroscopy indicate that Form III is a pseudopolymorphic form of 5-azacytidine, specifically a monohydrate. See Examples 6-7.

Form IV

Figure 4:
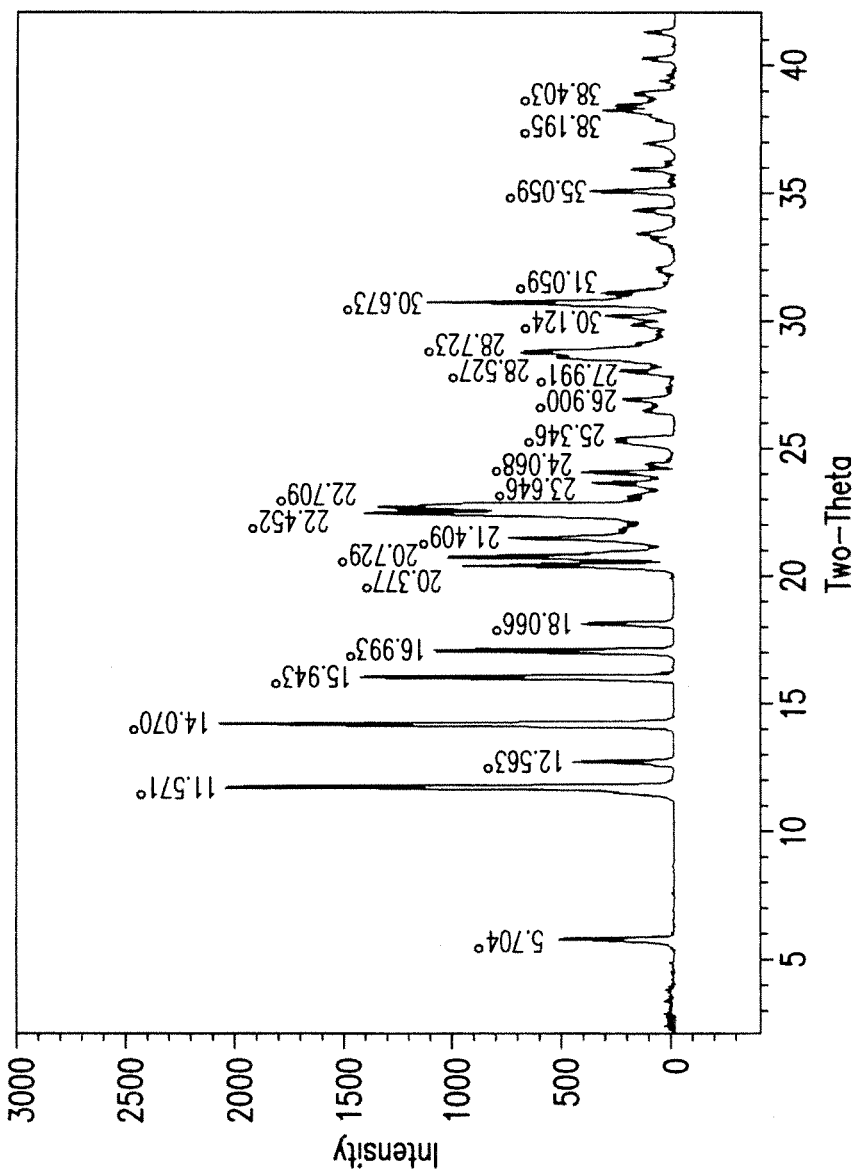
FIG. 4 presents the XRPD pattern of 5-azacytidine, Form IV, labeled with the most prominent 2θ angles (Cu Kα radiation).

Form IV is a novel crystalline form of 5-azacytidine. Form IV was recovered by slow recrystallization from a DMSO/toluene co-solvent system (see Example 2) or by fast recrystallization from the DMSO/chloroform co-solvent system (see Example 3). The XRPD powder pattern of Form IV is shown in FIG. 4 along with some of the 2θ values. Table 4 provides the most prominent 2θ angles, d-spacing and relative intensities for this crystalline material. The XRPD powder pattern for Form IV is distinctly different from that of any other form.

TABLE 4

5-azacytidine Form IV - the most prominent 2θ angles, d-spacing and relative intensities (Cu Kα radiation)

| 2θ Angle (°) | d-spacing (Å) | Relative Intensity |
|---|---|---|
| 5.704 | 15.408 | 24.9 |
| 11.571 | 7.642 | 97.8 |
| 12.563 | 7.040 | 22.2 |
| 14.070 | 6.289 | 100.0 |
| 15.943 | 5.555 | 67.4 |
| 16.993 | 5.213 | 51.0 |
| 18.066 | 4.906 | 20.1 |
| 20.377 | 4.355 | 44.7 |
| 20.729 | 4.281 | 49.0 |
| 21.484 | 4.132 | 36.30 |
| 21.803 | 4.073 | 11.2 |
| 22.452 | 3.957 | 66.7 |
| 22.709 | 3.913 | 64.0 |
| 23.646 | 3.760 | 17.3 |
| 24.068 | 3.695 | 19.4 |
| 25.346 | 3.526 | 12.0 |
| 25.346 | 3.511 | 12.5 |
| 26.900 | 3.312 | 11.0 |
| 27.991 | 3.185 | 11.4 |
| 28.527 | 3.126 | 25.7 |
| 28.723 | 3.106 | 34.1 |
| 30.124 | 2.964 | 14.7 |
| 30.673 | 2.912 | 53.6 |
| 31.059 | 2.877 | 15.7 |
| 35.059 | 2.557 | 18.1 |
| 38.195 | 2.354 | 15.0 |
| 38.403 | 2.342 | 12.6 |

Thermal analysis of Form IV is presented in Example 6.

Form V

Figure 5:
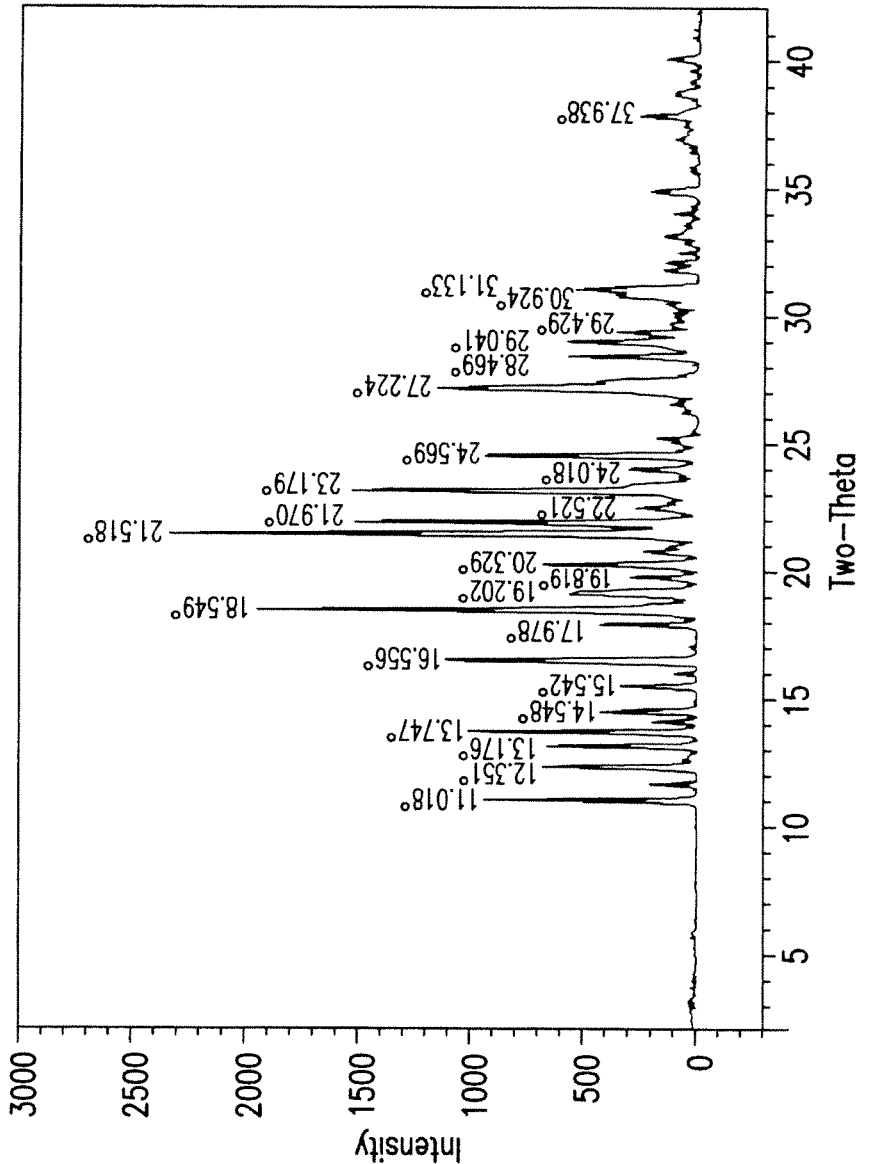
FIG. 5 presents the XRPD pattern of 5-azacytidine, Form V, labeled with the most prominent 2θ angles (Cu Kα radiation).
Figure 6:
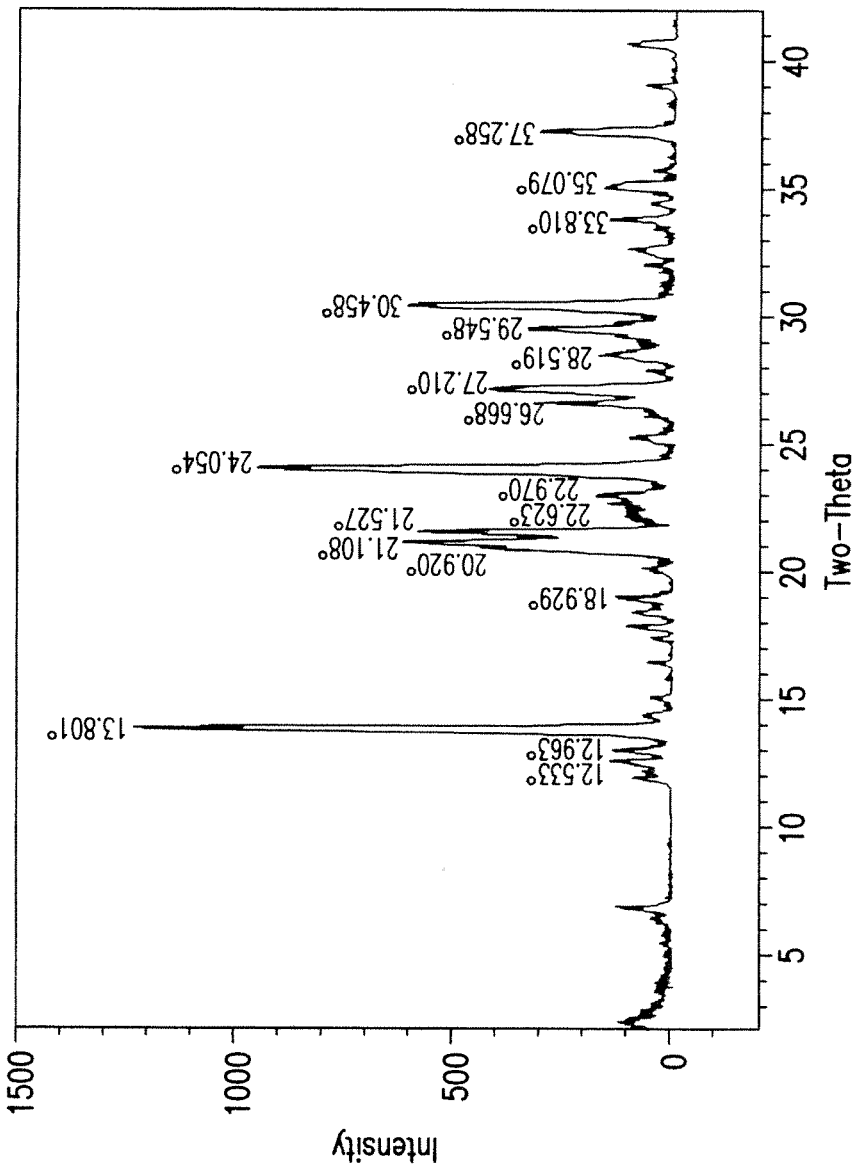
FIG. 6 presents the XRPD pattern of 5-azacytidine, Form VI, labeled with the most prominent 2θ angles (Cu Kα radiation).

Form V is a novel crystalline form of 5-azacytidine. Form V was recovered by fast recrystallization of 5-azacytidine from a DMSO/toluene co-solvent system (see Example 3). The XRPD powder pattern of Form V is shown in FIG. 5 along with some of the 2θ values. Table 5 provides the most prominent 2θ angles, d-spacing and relative intensities for this crystalline material. The XRPD powder pattern for Form V is distinctly different from that of any other form.

TABLE 5

5-azacytidine Form V - the most prominent 2θ angles, d-spacing and relative intensities (Cu Kα radiation)

| 2θ Angle (°) | d-spacing (Å) | Relative Intensity |
|---|---|---|
| 11.018 | 8.024 | 40.0 |
| 12.351 | 7.160 | 29.6 |
| 13.176 | 6.714 | 28.3 |
| 13.747 | 6.436 | 42.9 |
| 14.548 | 6.084 | 18.3 |
| 15.542 | 5.697 | 14.2 |
| 16.556 | 5.350 | 47.8 |
| 17.978 | 4.930 | 18.1 |
| 18.549 | 4.780 | 83.9 |
| 19.202 | 4.618 | 25.0 |
| 19.819 | 4.476 | 12.1 |
| 20.329 | 4.365 | 28.6 |
| 21.518 | 4.126 | 100.0 |
| 21.970 | 4.042 | 65.6 |
| 22.521 | 3.948 | 11.5 |
| 23.179 | 3.834 | 66.5 |
| 24.018 | 3.702 | 13.0 |
| 24.569 | 3.620 | 40.7 |
| 27.224 | 3.273 | 50.2 |
| 28.469 | 3.133 | 24.2 |
| 29.041 | 3.072 | 24.8 |
| 29.429 | 3.033 | 15.0 |
| 30.924 | 2.889 | 15.6 |
| 31.133 | 2.870 | 22.6 |
| 37.938 | 2.370 | 10.7 |

Thermal analysis indicates that Form V is a solvate. See Example 6.

Form VI

The drug product used in the aforementioned NCI investigation was typically prepared by lyophilizing a solution of 5-azacytidine and mannitol (1:1 w/w). The resultant drug product comprised 100 mg of 5-azacytidine and 100 mg mannitol as a lyophilized cake in a vial and was administered by subcutaneous injection as an aqueous suspension ("slurry"). XRPD analysis of retained samples of the drug product used in the NCI investigation revealed the existence of another polymorph, Form VI. The retained drug product samples comprised either Form VI alone, or a Form I/VI mixed phase. Table 6 provides the most prominent 2θ angles, d-spacing and relative intensities for Form VI.

TABLE 6

5-azacytidine Form VI - the most prominent 2θ angles, d-spacing and relative intensities (Cu Kα radiation)

| 2θ Angle (°) | d-spacing (Å) | Relative Intensity |
|---|---|---|
| 12.533 | 7.057 | 10.1 |
| 12.963 | 6.824 | 10.2 |
| 13.801 | 6.411 | 100.0 |
| 18.929 | 4.6843 | 10.0 |
| 20.920 | 4.243 | 34.2 |
| 21.108 | 4.205 | 49.4 |
| 21.527 | 4.125 | 47.0 |
| 22.623 | 3.922 | 10.7 |
| 22.970 | 3.869 | 13.8 |
| 24.054 | 3.697 | 77.8 |
| 26.668 | 3.340 | 23.0 |
| 27.210 | 3.275 | 33.7 |
| 28.519 | 3.127 | 12.9 |
| 29.548 | 3.021 | 27.2 |
| 30.458 | 2.932 | 50.3 |
| 33.810 | 2.649 | 11.6 |
| 35.079 | 2.556 | 12.6 |
| 37.528 | 2.411 | 24.7 |

Thermal analysis and proton ($^1$H) NMR spectroscopy of Form VI is presented in Examples 6-7.

Form VII

Figure 7:
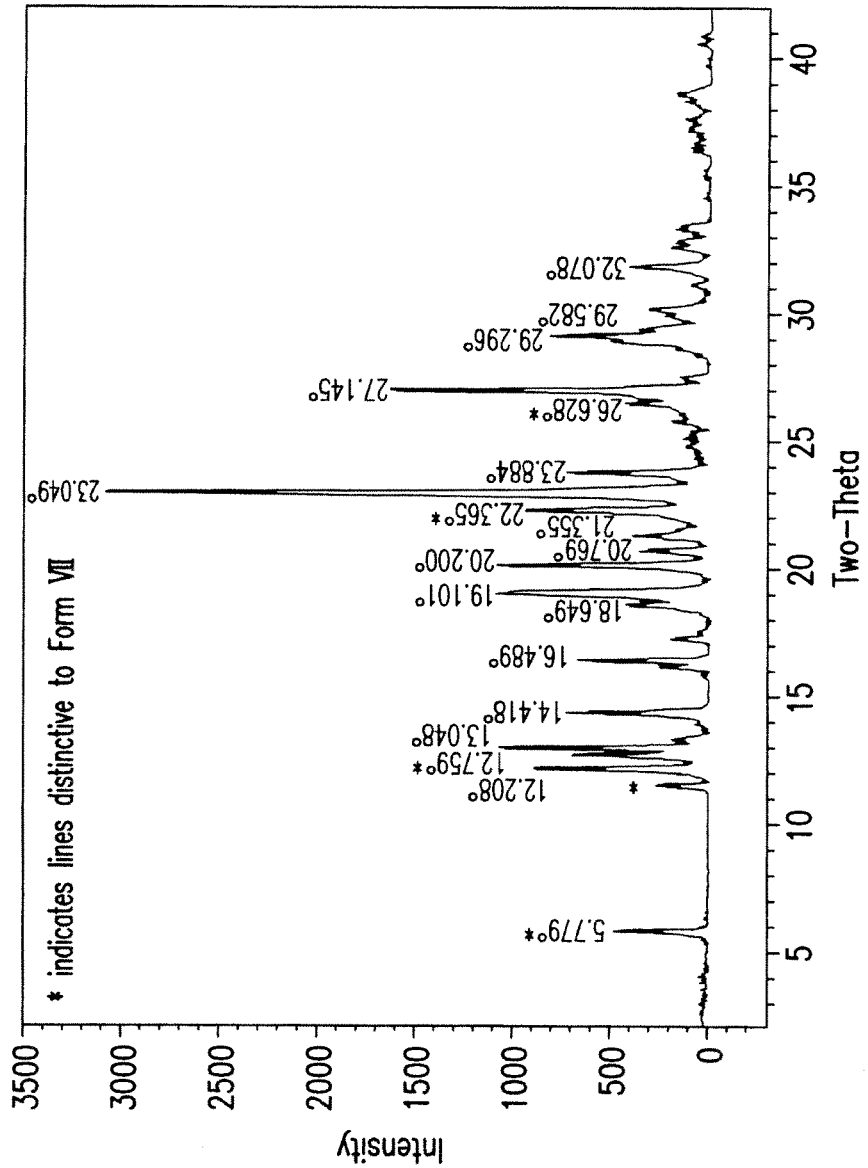
FIG. 7 presents the XRPD pattern of 5-azacytidine, mixed phase Form I and Form VII, labeled with the most prominent 2θ angles (Cu Kα radiation).

Form VII is a novel crystalline form of 5-azacytidine. Form VII was produced by fast recrystallization from a DMSO/methanol co-solvent system (see Example 3). Form VII was always isolated by this recrystallization method as a mixed phase with Form I. The XRPD powder pattern of mixed phase Forms I and VII is shown in FIG. 7 along with some of the 2θ values and the Form VII distinctive peaks indicated with asterisks. Table 7 provides the most prominent 2θ angles, d-spacing and relative intensities for this mixed phase. Form VII exhibits distinctive peaks at 5.8, 11.5, 12.8, 22.4 and 26.6° 2θ in addition to peaks displayed in the Form I XRPD powder pattern. The XRPD pattern for mixed phase Forms I and VII is distinctly different from that of any other form.

TABLE 7

5-azacytidine, mixed Forms I and VII - the most prominent 2θ angles, d-spacing and relative intensities (Cu Kα radiation)

| 2θ Angle (°) | d-spacing (Å) | Relative Intensity |
|---|---|---|
| 5.779 | 15.281 | 14.7 |
| 11.537 | 7.664 | 8.3 |
| 12.208 | 7.244 | 28.0 |
| 12.759 | 6.932 | 21.7 |
| 13.048 | 6.780 | 34.4 |
| 14.418 | 6.138 | 22.5 |
| 16.489 | 5.372 | 21.6 |
| 18.649 | 4.754 | 13.5 |
| 19.101 | 4.643 | 34.7 |
| 20.200 | 4.392 | 34.4 |
| 20.769 | 4.273 | 10.5 |
| 21.355 | 4.157 | 11.7 |
| 22.365 | 3.972 | 29.9 |
| 23.049 | 3.856 | 100.0 |
| 23.884 | 3.723 | 23.1 |
| 26.628 | 3.345 | 13.3 |
| 27.145 | 3.282 | 52.9 |
| 29.296 | 3.046 | 26.2 |
| 29.582 | 3.017 | 11.3 |
| 32.078 | 2.788 | 12.9 |

Thermal analysis of Form VII is presented in Example 6

Form VIII

Form VIII is a novel crystalline form of 5-azacytidine. Form VIII was recovered by recrystallizing 5-azacytidine Form I from a N-methyl-2-pyrrolidone (NMP) single solvent system (see Example 4). The XRPD powder pattern of Form VIII is shown in FIG. 8 along with some of the 2θ values. Table 8 provides the most prominent 2θ angles, d-spacing and relative intensities for this material. The XRPD pattern for Form VIII is distinctly different from that of any other form.

TABLE 8

5-azacytidine, Form VIII - the most prominent 2θ angles, d-spacing and relative intensities (Cu Kα radiation)

| 2θ Angle (°) | d-spacing (Å) | Relative Intensity |
|---|---|---|
| 6.599 | 13.384 | 2.9 |
| 10.660 | 8.292 | 2.2 |
| 12.600 | 7.020 | 23.4 |
| 13.358 | 6.623 | 2.6 |
| 15.849 | 5.587 | 2.0 |
| 17.275 | 5.129 | 4.2 |
| 20.243 | 4.383 | 5.8 |
| 20.851 | 4.257 | 7.8 |
| 21.770 | 4.079 | 74.4 |
| 22.649 | 3.923 | 32.1 |
| 25.554 | 3.483 | 100.0 |
| 25.740 | 3.458 | 7.8 |
| 29.293 | 3.046 | 3.8 |

TABLE 8-continued 5-azacytidine, Form VIII - the most prominent 2θ angles, d-spacing and relative intensities (Cu Kα radiation)

| 2θ Angle (°) | d-spacing (Å) | Relative Intensity |
|---|---|---|
| 32.148 | 2.782 | 8.8 |
| 35.074 | 2.556 | 7.4 |
| 38.306 | 2.348 | 2.5 |

Amorphous 5-azacytidine

Amorphous 5-azacytidine may be recovered from equilibrium saturated solutions of 5-azacytidine in propylene glycol, polyethylene glycol and DMSO. See Example 8.

Pharmaceutical Formulations

For the most effective administration of drug substance of the present invention, it is preferred to prepare a pharmaceutical formulation (also known as the "drug product") preferably in unit dose form, comprising one or more of the 5-azacytidine forms of the present invention and one or more pharmaceutically acceptable carrier, diluent, or excipient.

Such pharmaceutical formulation may, without being limited by the teachings set forth herein, include a solid form of the present invention which is blended with at least one pharmaceutically acceptable excipient, diluted by an excipient or enclosed within such a carrier that can be in the form of a capsule, sachet, tablet, buccal, lozenge, paper, or other container. When the excipient serves as a diluent, it may be a solid, semi-solid, or liquid material which acts as a vehicle, carrier, or medium for the 5-azacytidine polymorph(s). Thus, the formulations can be in the form of tablets, pills, powders, elixirs, suspensions, emulsions, solutions, syrups, capsules (such as, for example, soft and hard gelatin capsules), suppositories, sterile injectable solutions, and sterile packaged powders.

Examples of suitable excipients include, but are not limited to, starches, gum arabic, calcium silicate, microcrystalline cellulose, polyvinylpyrrolidone, cellulose, water, syrup, and methyl cellulose. The formulations can additionally include lubricating agents such as, for example, talc, magnesium stearate and mineral oil; wetting agents; emulsifying and suspending agents; preserving agents such as methyl- and propyl-hydroxybenzoates; sweetening agents; or flavoring agents. Polyols, buffers, and inert fillers may also be used. Examples of polyols include, but are not limited to: mannitol, sorbitol, xylitol, sucrose, maltose, glucose, lactose, dextrose, and the like. Suitable buffers encompass, but are not limited to, phosphate, citrate, tartrate, succinate, and the like. Other inert fillers which may be used encompass those which are known in the art and are useful in the manufacture of various dosage forms. If desired, the solid pharmaceutical compositions may include other components such as bulking agents and/or granulating agents, and the like. The compositions of the invention can be formulated so as to provide quick, sustained, controlled, or delayed release of the drug substance after administration to the patient by employing procedures well known in the art.

In certain embodiments of the invention, the 5-azacytidine forms(s) may be made into the form of dosage units for oral administration. The 5-azacytidine forms(s) may be mixed with a solid, pulverant carrier such as, for example, lactose, saccharose, sorbitol, mannitol, starch, amylopectin, cellulose derivatives or gelatin, as well as with an antifriction agent such as for example, magnesium stearate, calcium stearate, and polyethylene glycol waxes. The mixture is then pressed into tablets or filled into capsules. If coated tablets, capsules, or pulvules are desired, such tablets, capsules, or pulvules may be coated with a concentrated solution of sugar, which may contain gum arabic, gelatin, talc, titanium dioxide, or with a lacquer dissolved in the volatile organic solvent or mixture of solvents. To this coating, various dyes may be added in order to distinguish among tablets with different active compounds or with different amounts of the active compound present.

Soft gelatin capsules may be prepared in which capsules contain a mixture of the 5-azacytidine form(s) and vegetable oil or non-aqueous, water miscible materials such as, for example, polyethylene glycol and the like. Hard gelatin capsules may contain granules or powder of the 5-azacytidine polymorph in combination with a solid, pulverulent carrier, such as, for example, lactose, saccharose, sorbitol, mannitol, potato starch, corn starch, amylopectin, cellulose derivatives, or gelatin.

Tablets for oral use are typically prepared in the following manner, although other techniques may be employed. The solid substances are gently ground or sieved to a desired particle size, and a binding agent is homogenized and suspended in a suitable solvent. The 5-azacytidine form(s) and auxiliary agents are mixed with the binding agent solution. The resulting mixture is moistened to form a uniform suspension. The moistening typically causes the particles to aggregate slightly, and the resulting mass is gently pressed through a stainless steel sieve having a desired size. The layers of the mixture are then dried in controlled drying units for a pre-determined length of time to achieve a desired particle size and consistency. The granules of the dried mixture are gently sieved to remove any powder. To this mixture, disintegrating, anti-friction, and anti-adhesive agents are added. Finally, the mixture is pressed into tablets using a machine with the appropriate punches and dies to obtain the desired tablet size.

In the event that the above formulations are to be used for parenteral administration, such a formulation typically comprises sterile, aqueous and non-aqueous injection solutions comprising one or more 5-azacytidine forms for which preparations are preferably isotonic with the blood of the intended recipient. These preparations may contain anti-oxidants, buffers, bacteriostats, and solute; which render the formulation isotonic with the blood of the intended recipient. Aqueous and non-aqueous suspensions may include suspending agents and thickening agents. The formulations may be present in unit-dose or multi-dose containers, for example, sealed ampules and vials. Extemporaneous injection solutions and suspensions may be prepared from sterile powders, granules, and tablets of the kind previously described.

Liquid preparations for oral administration are prepared in the form of solutions, syrups, or suspensions with the latter two forms containing, for example, 5-azacytidine polymorph(s), sugar, and a mixture of ethanol, water, glycerol, and propylene glycol. If desired, such liquid preparations contain coloring agents, flavoring agents, and saccharin. Thickening agents such as carboxymethylcellulose may also be used.

As such, the pharmaceutical formulations of the present invention are preferably prepared in a unit dosage form, each dosage unit containing from about 5 mg to about 200 mg, more usually about 100 mg of the 5-azacytidine form(s). In liquid form, dosage unit contains from about 5 to about 200 mg. more usually about 100 mg of the 5-azacytidine form(s). The term "unit dosage form" refers to physically discrete units suitable as unitary dosages for human subjects/patients or other mammals, each unit containing a predetermined quantity of the 5-azacytidine polymorph calculated to produce the desired therapeutic effect, in association with preferably, at least one pharmaceutically acceptable carrier, diluent, or excipient.

The following examples are provided for illustrative purposes only, and are not to be construed as limiting the scope of the claims in any way.

EXAMPLES

Example 1

Prior Art Procedure for Synthesis of 5-azacytidine Drug Substance

Using commercially available 5-azacytosine (1) and 1,2,3, 5-Tetra-O-β-acetyl-ribofuranose (2) (RTA), 5-azacytidine (3) may be synthesized according to the pathway below.

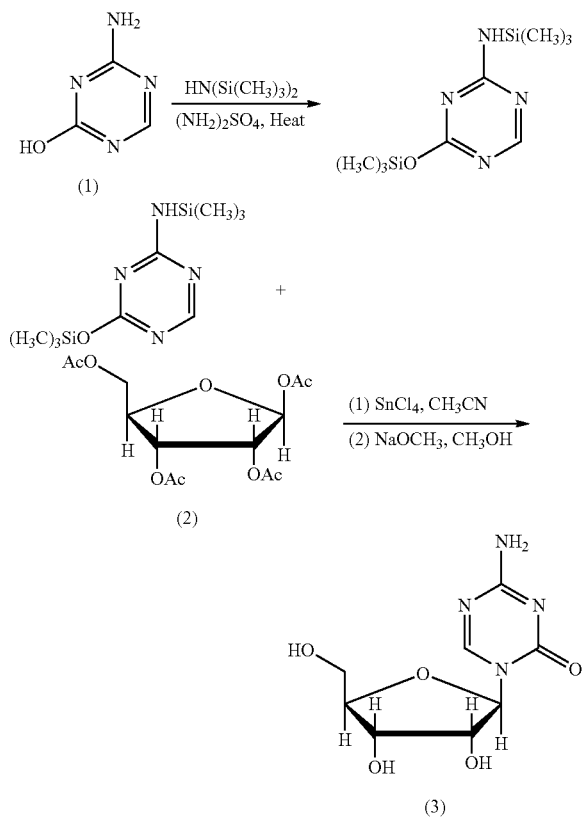

The crude synthesis product is dissolved in DMSO (preheated to about 90° C.), and then methanol is added to the DMSO solution. The co-solvent mixture is equilibrated at approximately −20° C. to allow 5-azacytidine crystal formation. The product is collected by vacuum filtration and allowed to air dry.

Example 2

Slow Recrystallization from DMSO/toluene

Dimethyl sulfoxide (DMSO) was used as the primary solvent to solubilize Form I of 5-azacytidine and toluene was used as the co-solvent as follows. Approximately 250 mg of 5-azacytidine was dissolved with approximately 5 mL of DMSO, preheated to approximately 90° C., in separate 100-mL beakers. The solids were allowed to dissolve to a clear solution. Approximately 45 mL of toluene, preheated to approximately 50° C., was added to the solution and the resultant solution was mixed. The solution was covered and allowed to equilibrate at ambient conditions. The product was collected by vacuum filtration as white crystals using a Buchner funnel. The collected product was allowed to air dry.

Example 3

Fast Recrystallization from DMSO/methanol, DMSO/toluene, and DMSO/chloroform

Approximately 250 mg of 5-azacytidine was dissolved with approximately 5 mL of DMSO as the primary solvent, preheated to approximately 90° C., in separate 100-mL beakers. The solids were allowed to dissolve to a clear solution. Approximately 45 mL of the selected co-solvent (methanol, toluene, or chloroform), preheated to approximately 50° C., was added to the solution and the resultant solution was mixed. The solution was covered and placed in a freezer to equilibrate at approximately −20° C. to allow crystal formation. Solutions were removed from the freezer after crystal formation.

The product from the methanol and toluene solutions was collected by vacuum filtration using a Buchner funnel. The resulting white crystalline product was allowed to air dry.

The chloroform product was too fine to be collected by vacuum filtration. Most of the solvent was carefully decanted from the chloroform solution and the solvent from the resultant slurry was allowed to evaporate at ambient temperature to dryness. The chloroform solution evaporated to a white product. Note that fast recrystallization using the DMSO/methanol co-solvent system has typically been used to prepare 5-azacytidine drug substance in the prior art (see the last step of the procedure provided in Example 1).

Example 4

Fast Recrystallization N-methyl-2-pyrrolidone (NMP) Single Solvent System

Approximately 500 mg of 5-azacytidine was dissolved with approximately 5 mL of NMP, preheated to approximately 90° C., in separate 50-mL beakers. The solids were allowed to dissolve to a clear solution. The solution was covered and placed in a freezer to equilibrate at approximately −20° C. to allow crystal formation. Solutions were removed from the freezer after crystal formation, equilibrated at ambient temperature. The product was collected by vacuum filtration using a Buchner funnel. The collected product was allowed to air dry.

Example 5

X-Ray Powder Diffraction of 5-azacytidine

X-ray powder diffraction patterns for each sample were obtained on a Scintag XDS 2000 or a Scintag $X_2$ θ/θ diffractometer operating with copper radiation at 45 kV and 40 mA using a Kevex Psi Peltier-cooled silicon detector or a Thermo ARL Peltier-cooled solid state detector. Source slits of 2 or 4 mm and detector slits of 0.5 or 0.3 mm were used for data collection. Recrystallized material was gently milled using an agate mortar and pestle for approximately one minute. Samples were placed in a stainless steel or silicon sample holder and leveled using a glass microscope slide. Powder diffraction patterns of the samples were obtained from 2 to 42° 2θ at 1°/minute. Calibration of the $X_2$ diffractometer is verified annually using a silicon powder standard. Raw data files were converted to ASCII format, transferred to an IBM compatible computer and displayed in Origin® 6.1 for Windows.

XRPD of a single sample of 5-azacytidine produced according to the method of Example 1 revealed that this sample consisted of Form I of 5-azacytidine.

NCI retained drug substance samples were also analyzed. These samples were all previously synthesized and recrystallized according to the method of Example 1 and were stored at 5° C. since production. XRPD revealed some retained samples are comprised of Form I alone, whereas other retained samples contain a mixed phase of Form I and a different polymorph, termed Form II.

XRPD of NCI retained drug product samples revealed the existence of Form VI in some samples. In those samples, Form VI was present as a mixed phase with Form I.

XRPD of the recrystallized 5-azacytidine obtained in Example 2 revealed that slow recrystallization from a DMSO/toluene system produced Form IV. XRPD of the recrystallized 5-azacytidine obtained in Example 3 revealed that fast recrystallization from a DMSO/chloroform system produced Form IV, fast recrystallization from a DMSO/toluene system produced Form V, and fast recrystallization from a DMSO/methanol system produced mixed phased Form I/Form VII. XRPD of the recrystallized 5-azacytidine obtained in Example 4 revealed that the N-methyl-2-pyrrolidone solvent system produced Form VIII.

Example 6

Thermal Analysis of 5-azacytidine

Differential Scanning calorimetry (DSC) measurements for each sample were collected using a Perkin Elmer Pyris 1 DSC system equipped with an Intracooler 2P refrigeration unit. The Pyris 1 DSC was purged with nitrogen. Calibration was performed prior to analysis using an Indium standard at a 10° C. minute heating rate. Each sample was gently ground in an agate mortar and pestle. Approximately 1-3 mg of the sample were individually sealed in a Perkin Elmer 30-µL universal aluminum pan with holes in the lid. Samples were heated from 25° C. to 250° C. or 350° C. at 10° C./minute.

Thermogravimetric Analysis (TGA) measurements for each sample were collected using a Perkin Elmer TGA 7 purged with nitrogen at approximately 20 cc/minute. A 100-mg standard weight and nickel metal were used to verify balance and temperature calibrations, respectively. Samples were heated from 25° C. to 250° C. or 300° C. at 10° C./minute.

Capillary melting point (MP) measurements were made using an Electrothermal 9300 melting point apparatus. A heating rate of 10° C./minute was used from set point temperatures described in individual discussions. Visual melting points are reported as an average of triplicate determinations.

The results are as follows:
Form I
TGA showed a weight loss of 0.23% between ambient and 150° C., which indicates that it is anhydrous. DSC exhibited a single event with an onset of 227.0° C.

A capillary melting point determination was performed in triplicate on a sample of Form I of 5-azacytidine. The sample was visually observed to decompose without melting at about 215° C. using a 10° C. heating rate and a starting temperature of 200° C. Thus, the DSC event results from decomposition of 5-azacytidine.

Form I/II Mixed Phase

The TGA for the Form I/II mixed phase showed a weight loss of 1.16% between ambient temperature and 150° C. The DSC analysis exhibited a single event with an onset at 229.8° C. The decomposition of the mixed phase was consistent with that observed for 5-azacytidine Form I.

Form III

The TGA showed a weight loss of between 6.56% and 8.44% when the temperature was raised from ambient and 150° C. The loss is close to the theoretical amount of moisture, 6.9%, that 5-azacytidine monohydrate would have. The DSC analysis exhibited an endotherm, which is in the range associated with solvent loss, and a higher temperature event. The endotherm exhibited an onset temperature in the range of 86.4-89.2° C., peak temperatures in the range of 95.8-97.0° C. and Δ H values in the range of 73.1-100.5 J/g. The higher temperature event had onset temperatures in the range 229.1-232.1° C. and was consistent with the decomposition observed for 5-azacytidine Form I.

5-azacytidine Form III was heated at 105° C. for 4 hours in an attempt to dehydrate the material. The material did not change its physical appearance during heating. TGA was used to measure the water content of Form III before and after drying. The initial amount of moisture present in Form III was 6.31% and was <0.1% after drying. The XRPD powder pattern for dehydrated Form III matches that of Form I. Thus, Form III dehydrates to Form I.

Form IV

The TGA showed a weight loss of 21.80% between ambient temperature and 150° C., which does not correspond to the solvent content for any simple solvates. It is not known whether crystalline Form IV is a polymorph or a pseudopolymorph.

The DSC analysis exhibited two endotherms and a higher temperature event. The two endotherms are in the range that is associated with solvent loss. The first endotherm exhibited an onset temperature of 87.6° C., a peak temperature of 90.1° C. and Δ H value of 98.3 J/g. The second endotherm exhibited an onset temperature of 136.0° C., a peak temperature of 139.0° C. and Δ H value of 81.8 J/g. The higher temperature event had an onset temperature of 230.6° C. and was consistent with the decomposition that was observed for 5-azacytidine Form I.

Form V

TG A showed a weight loss of 21.45% between ambient and 150° C., which does not correspond to the solvent content for any simple solvate. The DSC analysis exhibited two merged endotherms, a single endotherm and a higher temperature event. The three endotherms are in the range that is associated with solvent loss. The two merged endotherms exhibit onset temperatures of 66.6 and 68.0° C. The single endotherm exhibited an onset temperature of 88.7° C., a peak temperature of 121.5° C. and a Δ H value of 180.3 J/g. The higher temperature event had onset temperature of 230.7° C. and was consistent with the decomposition that was observed for 5-azacytidine Form I.

Form VI

TGA showed a weight loss of 1.10% between ambient temperature and 150° C. The DSC analysis exhibited a small endotherm, an exotherm and a higher temperature event. The small endotherm exhibited an onset temperature of 57.8° C., a peak temperature of 77.0° C. and a Δ H value of 55.7 J/g. The exotherm exhibited an onset temperature of 149.3° C., a peak temperature of 157.1° C. and an Δ H value of −17.9 J/g. The higher temperature event had an onset temperature of 234.7° C. and was consistent with the decomposition observed for 5-azacytidine Form I.

Form VII

TGA showed a weight loss of 2.45% between ambient temperature and 150° C. The DSC analysis exhibited a minor endotherm and a higher temperature event. The minor endotherm had an onset temperature of 63.3° C., a peak temperature of 68.3° C. and a Δ H value of 17.1 J/g. The higher temperature event had an onset temperature of 227.2° C. and is consistent with the decomposition observed for 5-azacytidine Form I.

Example 7

Nuclear Magnetic Resonance (NMR) Analysis of Form III and Form VI 5-azacytidine is know to be labile in water. Since Form III is found in equilibrium saturated solutions and Form VI is produced by the lyophilization of 5-azacytidine solution. it was of interest to examine the purity of these 5-azacytidine forms using NMR. The proton ($^1$H) NMR spectra of Form III and Form VI were both consistent with the structure of 5-azacytidine in all essential details.

Example 8

Polymorphic Form Conversion of 5-azacytidine

Form I of 5-azacytidine was added to various solvents in sufficient quantities to form a slurry, and the slurry allowed to equilibrate for a period of time. The solid material that was present in the slurry was recovered, dried, and analyzed using XRPD (according to the XRPD protocol included in Example 5) with the aim of detecting new polymorphs and pseudopolymorphs during the transition to the dissolved state. Samples equilibrated for 19 hours in saline, 5% dextrose, 5% tween 80, water-saturated octanol, ethanol/water (50/50) and water alone resulted in a distinctly different form of 5-azacytidine, designated Form III (see below). Samples equilibrated for 19 hours in acetone, methyl ethyl ketone, and ethanol resulted in materials identified as Form I. Samples equilibrated for 19 hours in propylene glycol, polyethylene glycol and DMSO resulted in amorphous materials. The results are summarized in Table 9.

TABLE 9

X-ray Powder Diffraction Analysis Results for Solubility Samples: Form Assignment (Cu Kα radiation)

| Solvent | XRPD Pattern Assignment |
|---|---|
| Normal Saline | Form III |
| 5% Dextrose | Form III |
| Acetone | Form I |
| Propylene glycol | Amorphous |
| Polyethylene glycol | Amorphous |
| Methyl ethyl ketone | Form I |
| 5% Tween 80 | Form III |
| DMSO | Amorphous |
| Water-saturated Octanol | Form III |
| Ethyl alcohol | Form I |
| 50/50 EtOH/DI Water | Form III |
| DI Water | Form III |

The conversion of other forms of 5-azacytidine was also studied. Specifically, a Form I/II mixed phase, Form VI (the lyophilized drug product used in the prior art NCI drug trials), a Form I/VI mixed phase, and a Form I/VII mixed phase were weighed into individual small glass beakers and water was pipetted into each beaker. The sample size and water volume were scaled to maintain an approximate 25 mg/mL ratio. The resultant slurry was allowed to equilibrate for 15 minutes. After equilibration, the sample was filtered and the solid material was dried and analyzed using XRPD. In each case, Form III of 5-azacytidine was observed. The results indicate that all forms of 5-azacytidine convert to Form III during the transition to the dissolved state in water. Thus, when an 5-azacytidine suspension ("slurry") was administered to patients in the aforementioned NCI investigation, the patients received both 5-azacytidine in solution, and Form III of 5-azacytidine.

What is claimed is:

1. A pharmaceutical composition for oral administration comprising Form I and Form II of 5-azacytidine substantially free of other forms of 5-azacytidine, wherein the pharmaceutical composition is a tablet or a capsule.

2. The pharmaceutical composition of claim 1, wherein the Form II of 5-azacytidine is characterized by X-Ray Powder Diffraction peaks at approximately 13.5, 17.6, and 22.3 degrees 2θ.

3. The pharmaceutical composition of claim 1, wherein the Form I and Form II of 5-azacytidine is characterized by X-Ray Powder Diffraction peaks at the following 2θ angles:

| 2θ Angle (degree) |
| --- |
| 12.244 |
| 13.082 |
| 13.458 |
| 14.452 |
| 16.521 |
| 17.648 |
| 18.677 |
| 19.093 |
| 20.231 |
| 21.353 |
| 22.309 |
| 23.070 |
| 23.909 |
| 26.641 |
| 26.813 |
| 27.158 |
| 29.309 |
| 29.609 |
| 30.384 |
| 32.074. |

4. The pharmaceutical composition of claim 1, wherein the Form I and Form II of 5-azacytidine is characterized by an X-ray powder diffraction pattern corresponding to the representative X-Ray Powder Diffraction Pattern provided in FIG. 2.

5. The pharmaceutical composition of claim 1, wherein the Form I and Form II of 5-azacytidine has a thermogravimetric analysis thermogram comprising a weight loss of about 1.16% between ambient temperature and 150° C.

6. The pharmaceutical composition of claim 1, wherein the Form I and Form II of 5-azacytidine has a differential scanning calorimetry thermogram comprising a thermal event with an onset at about 229.8° C.

7. The pharmaceutical composition of claim 1, which is in a single unit dosage form.

8. The pharmaceutical composition of claim 1, which is a tablet.

9. The pharmaceutical composition of claim 1, which is a capsule.

10. The pharmaceutical composition of claim 1, which contains between about 5 mg and about 200 mg of 5-azacytidine.

11. The pharmaceutical composition of claim 10, which contains about 100 mg of 5-azacytidine.

12. The pharmaceutical composition of claim 1, which further comprises a carrier, diluent, or excipient.

13. The pharmaceutical composition of claim 12, which comprises at least one of mannitol, microcrystalline cellulose, and magnesium stearate.

* * * * *